United States Patent [19]

Schoemaker et al.

[11] Patent Number: 4,837,167
[45] Date of Patent: Jun. 6, 1989

[54] IMMUNOASSAY FOR MULTI-DETERMINANT ANTIGENS USING HIGH-AFFINITY IGM

[75] Inventors: Hubert J. P. Schoemaker, Devon, Pa.; Jack R. Wands, Waban, Mass.; Barbara L. Westrick, Flourtown; Vincent R. Zurawski, Jr., West Chester, both of Pa.

[73] Assignees: Centocor, Inc., Malvern, Pa.; The General Hospital Corporation, Boston, Mass.; Centocor, Inc., Malvern, Pa.

[21] Appl. No.: 603,415

[22] Filed: Apr. 24, 1984

Related U.S. Application Data

[63] Continuation-in-part of Ser. No. 230,175, Jan. 30, 1981.

[51] Int. Cl.$^4$ .................. G01N 33/537; G01N 33/576; G01N 33/577; C12Q 1/70
[52] U.S. Cl. ..................................... 436/513; 436/518; 436/536; 436/540; 436/542; 436/548; 436/804; 436/819; 436/820; 435/5; 435/7; 935/107; 935/108; 935/110; 530/387; 530/806; 424/86
[58] Field of Search ............... 436/513, 518, 528, 536, 436/540, 542, 548, 804, 811, 815, 819, 823; 435/4, 5, 7, 68, 172.2; 935/107, 108, 110; 424/86

[56] References Cited

U.S. PATENT DOCUMENTS

| | | | |
|---|---|---|---|
| 4,244,940 | 1/1981 | Jeong et al. | 23/230 B |
| 4,271,145 | 6/1981 | Wands et al. | 424/85 |
| 4,361,647 | 11/1982 | Remington et al. | 435/7 |
| 4,376,110 | 3/1983 | David et al. | 436/513 |

FOREIGN PATENT DOCUMENTS

| | | |
|---|---|---|
| 0038642 | 10/1981 | European Pat. Off. . |
| 0045103 | 3/1982 | European Pat. Off. . |
| 0048357 | 3/1982 | European Pat. Off. . |
| 8201072 | 4/1982 | PCT Int'l Appl. . |
| 8202661 | 8/1982 | PCT Int'l Appl. . |
| 2074727 | 11/1981 | United Kingdom . |

OTHER PUBLICATIONS

Wands, J. R. et al., Proc. Natl. Acad. Sci., USA, vol. 78(2), pp. 1214–1218, (2–1981).
Wands, J. R. et al., Gastroenterology, vol. 80, pp. 225–232(1981), See Table 5.
Wands, J. R. et al., Gastroenterology, vol. 79,5, part 2, p. 1063, (11–1980), AASLD Abstract.
Ehrlich, P. H. et al., J. Immunology, vol. 128(6), pp. 2709–2713, (6–1982).
Crothers, D. M. et al., Immunochemistry, vol. 9, pp. 341–357, (1972).
Eisen, H. M., *Immunology*, pp. 416–418, Harper & Row, publishers, Hagerstown, MD, (1974).
Berzofsky, J. A. et al., Biochemistry, vol. 15(10), pp. 2113–2121, (1976).
Votilla, M. et al., J. Immunological Methods, vol. 42, pp. 11–15, (1981).
David, G. S. et al., Clin. Chem., vol. 27(9), pp. 1580–1585, (1981).

*Primary Examiner*—Margaret Moskowitz
*Assistant Examiner*—Jeff P. Kushan
*Attorney, Agent, or Firm*—Hamilton, Brook, Smith & Reyonlds

[57] ABSTRACT

A simultaneous sandwich immunoassay employing high-affinity monoclonal antibodies is disclosed. This simultaneous sandwich assays has surprising sensitivity compared to forward and reverse sandwich assays for the detection of multi-determinant antigens such as hepatitis B surface antigen.

15 Claims, No Drawings

IMMUNOASSAY FOR MULTI-DETERMINANT ANTIGENS USING HIGH-AFFINITY IGM

RELATED APPLICATION

This is a continuation-in-part of Ser. No. 230,175, filed Jan. 30, 1981.

TECHNICAL FIELD

This invention is in the field of immunology and particularly relates to an immunoassay for the detection of multi-determinant antigens.

BACKGROUND ART

The desirability of having an immunoassay capable of being employed by hospitals and clinical laboratories for the early detection of viral infections has been widely recognized. The need for such an assay can be illustrated, for example, by acute hepatitis B, one form of the various hepatitis viral infections. Acute hepatitis B causes significant mortality and morbidity and chronic infection with this virus is also associated with hepatocellular carcinoma, chronic active hepatitis and cirrhosis. In view of this need, much research has been devoted to the development of immunoassays capable of detecting viral antigens such as hepatitis B surface antigen (HBsAg), the viral marker for hepatitis B, in the blood stream of patients.

Generally, the immunoassays which have been developed to date can be classified as radioimmunoassays (RIA) or immunoradiometric assays (IRMA). In a RIA, the amount of antigen present in a sample is measured indirectly employing a limited amount of antibody to compete for labeled antigen. In an IRMA, antigen is assayed directly by reacting the antigen with excess labeled antibody.

In one class of IRMA assays, the unknown antigen is insolubilized and reacted with labeled antibody. When the antigen is insolubilized by reaction with solid-phase antibody, the assay is termed a "two-site IRMA", "junction test", or "sandwich assay". Sandwich assays are further classified according to their methodology as forward, reverse or simultaneous sandwich assays.

Heretofore, the most widely used immunoassay for viral hepatitis B has been the forward sandwich assay. In this assay, a patient sample containing HBsAg is initially incubated with a solid-phase immunoadsorbent containing immobilized antibody for HBsAg. Incubation is continued for a sufficient period of time to allow HBsAg in the patient sample to bind to immobilized antibody on the solid-phase immunoadsorbent. After this first incubation, the solid-phase immunoadsorbent is separated from the incubation mixture and washed to remove excess antigen and other interfering substances, such as non-specific binding proteins, which also may be present in the patient sample. The solid-phase immunoadsorbent containing HBsAg bound to immobilized antibody is subsequently incubated for a second time with labeled antibody capable of binding to HBsAg, which is multivalent. After the second incubation, another wash is performed to remove unbound labeled antibody from the solid-phase immunoadsorbent thereby removing non-specifically bound labeled antibody. Labeled antibody bound to the solid phase immunoadsorbent is then detected and the amount of labeled antibody detected serves as a direct measure of the amount of HBsAg present in the original patient sample. Such forward sandwich assays are described in the patent literature, and in particular, in U.S. Pat. Nos. 3,867,517 and 4,012,294, issued to Chung-Mei Ling.

Despite their widespread use, forward sandwich assays do have certain inherent disadvantages. For example, the requirement to perform two separate incubations as well as two separate washings means that the assay is relatively time-consuming and requires a number of manipulative operations which must be performed by skilled technicians thereby making the forward sandwich assay relatively costly. In addition, the kinetics in the second incubation are relatively slow since labeled antibody must react in this step with antigen bound to antibody immobilized on the solid-phase immunoadsorbent.

The reverse sandwich immunoassay was developed to overcome some of the disadvantages of the forward sandwich assay. In a reverse sandwich assay, the patient sample is initially incubated with labeled antibody after which the solid-phase immunoadsorbent containing immobilized antibody is added and a second incubation is carried out. Thus, the initial washing step of a forward sandwich assay is not required, although a wash is performed after the second incubation period. The major advantages to the reverse sandwich assay compared to the forward sandwich assay are the elimination of the first wash step and the improvement in kinetics of reaction since the labeled antibody and antigen in the patient serum are initially incubated together. Thus, for a total incubation period less than that required to reach equilibrium, it would be expected that the sensitivity of the reverse assay would be higher than that of the forward assay. A reverse sandwich assay has been described in the patent literature in U.S. Pat. No. 4,098,876, issued to Roger N. Piasio et al.

Although reverse sandwich assays have potential advantages over forward sandwich assays, they still require two separate incubation periods and one washing.

Simultaneous sandwich assays, although known, have not found widespread use. In a simultaneous sandwich assay, the patient sample, immunoadsorbent having immobilized antibody thereon, and labeled antibody are incubated simultaneously in one incubation step. Although offering certain potential advantages due to the single incubation and lack of washing steps required, simultaneous sandwich assays have previously been found to be less sensitive and reliable than forward and reverse sandwich assays. This would be expected, of course, since the patient sample often contains many non-specific binding molecules, such as proteins, which are not washed from the assay as they are in the forward sandwich assay.

DISCLOSURE OF THE INVENTION

This invention relates to a simultaneous sandwich assay for detecting the presence of multi-determinant antigens in liquid samples, such as the blood of a patient. As pointed out above, in a simultaneous sandwich assay, the patient sample is incubated simultaneously with both an immunoadsorbent containing immobilized antibody for the antigen and labeled antibody for the antigen. Thereafter, labeled antibody bound to the immunoadsorbent is detected as an indication of the amount of antigen present in the patient sample.

In a broad sense, this invention comprises the improvement of employing high-affinity monoclonal antibodies for both immobilized antibody and labeled antibody in a simultaneous sandwich assay. These high-affinity antibodies can comprise either monoclonal IgG or monoclonal IgM antibodies. One preferred embodiment of this simultaneous sandwich assay employs high-affinity monoclonal IgM antibody for HBsAg for both immobilized and labeled antibody in a particularly sensitive assay for viral hepatitis B.

The simultaneous sandwich assay described herein allows the realization of the previously recognized potential advantages of a simultaneous sandwich assay. For example, the assay is simpler and requires less steps since there is only one incubation and since no washing steps are required. This reduces the amount of skilled technician time required which, in turn, reduces the cost of performing the assay.

More importantly, however, is the surprising sensitivity which can be obtained when monoclonal antibodies are employed in a simultaneous sandwich assay. For example, for total incubation times which are comparable, it has been found that the simultaneous sandwich assay described herein can be more sensitive than either a forward or reverse assay for the detection of HBsAg.

Another unexpected advantage of the assay described herein is the wide range of antigen concentration which can be detected, despite the fact that only one incubation is employed and no washing steps are employed. For example, it has been found that this assay is capable of detecting HBsAg over a greater than ten million-fold dilution range.

BEST MODE FOR CARRYING OUT THE INVENTION

The simultaneous sandwich assay described herein is useful for the detection of multi-determinant antigens. By "multi-determinant," it is meant that the antigen contains a plurality of the same antigenic determinant (epitope). Sometimes, such antigens have also been referred to in the literature as "polydeterminant" antigens, but the terminology "multi-determinant" will be used herein to describe such antigens.

Another term used to describe antigenic determinants is the term "multivalent." The term "multivalent" is used herein to mean that the antigen has a plurality of different antigenic determinants or epitopes thereon.

Many viral antigens are both multi-determinant and multivalent. For example, the hepatitis B virus is known to be a complex 42 nanometer (nm) particle having at least three well defined antigens. These include the hepatitis B core antigen (HBcAg), the hepatitis B e antigen (HBeAg), and the hepatitis B surface antigen (HBsAg).

The HBsAg antigen is a high molecular weight complex protein which occurs on the surface of the intact hepatitis B virus. However, HBsAg is also present in the blood of patients infected with hepatitis B as a circulating 22 nm particle or filamentous form. Because of its presence in the bloodstream of infected patients, HBsAg has become the most widely employed specific viral marker for acute and chronic hepatitis B infection.

HBsAg has been found in patient serum samples at concentrations of up to about 800 micrograms/ml. Data indicate, however, that serum concentrations as low as about 50 pg/ml can be infectious. This represents an extraordinarily wide range for an assay to cover.

Although much of the description of the simultaneous sandwich assay described herein is presented in terms of the detection of HBsAg, it should be recognized that the assay itself is suitable for the detection of any multi-determinant antigen. This includes other viral antigens which are multi-determinant, such as Herpes Simplex viruses I and II, Herpes Virus Zoster, Cytomegalovirus, Epstein-Barr virus, Papova viruses such as BK or JC virus, measles virus, rubella virus, influenza or parainfluenza viruses, etc. Viral subunits, such as virus capsids, can also be detected as long a such subunits are multi-determinant. Additionally, antigens need not be viral in nature to be multi-determinant and the simultaneous sandwich assay described herein is suitable for detecting such non-viral multi-determinant antigens. Such non-viral multi-determinant antigens might include, for example, cells, immune complexes, membrane preparations, bacteria, etc.

Such multi-determinant antigens are assayed in a liquid sample. Often, the liquid sample is a sample of a patient's blood or a blood component such as plasma or serum. Other liquid samples, such as urine, could of course be assayed by the simultaneous sandwich assay described herein.

In this assay, high-affinity monoclonal antibodies are employed for both immobilized antibody bound to an immunoadsorbent as well as for labeled antibody.

The term "high-affinity" is employed herein to mean that the antibody has an affinity binding constant (K) of greater than $10^9 n^{-1}$, and preferably greater than $10^{11} n^{-1}$. Binding constants are determined from Scatchard plots employing known techniques, and are, of course, determined for the whole antigen and antibody molecules rather than on a per site basis.

The term "monoclonal" means that the antibody has been produced by a cell line cloned from a single antibody producing cell. Monoclonal antibodies are extraordinarily pure, uniform and reproducable since each antibody is effective against a single antigenic determinant.

Monoclonal antibodies can be obtained in significant quantities from hybridoma cells. Hybridoma cells are fused cells resulting from the fusion of antibody producing cells with tumor cells. The initial work relating to the production of such hybridoma cells was done by Cesar Milstein and George Köhler employing mouse myeloma cells with spleen cells taken from mice immunized with sheep red blood cells. See, Köhler et al., *Eur. J. Immunol.*, 6, 511-19 (1976); Köhler et al., *Nature*, 256, 495-7 (1975); and Milstein, *Scientific American*, 243 (4), 66-74 (1980).

More recently, Hilary Koprowski and collegues have extended the original hybridoma work by developing hybridoma cell lines capable of producing monoclonal antibodies against specific viruses and tumors. See, U.S. Pat. Nos. 4,196,265 and 4,172,124, respectively. Even more recently, the hybridoma technology has been further extended to produce hybridoma cell lines capable of producing monoclonal antibodies to hepatitus virus. See U.S. Pat. No. 4,271,145 in the names of Jack R. Wands and Vincent R. Zurawski. It has also been recently discovered that monoclonal IgM antibodies produced from hybridoma cell lines can be employed in certain immunoassays to improve the sensitivity and specificity thereof. See U.S. application Ser. No. 188,735, filed Sept. 19, 1980, in the names of Jack R. Wands, Vincent R. Zurawski, and Huber J. P. Schoemaker.

Thus, the general scientific and patent literature include many descriptions of hybridoma cell lines and monoclonal antibodies produced from such cell lines. These teachings are relied on in general herein, and specifically the teachings of each of the heretofore mentioned articles and patents relating to hybridoma cell lines and/or monoclonal antibodies are hereby incorporated by reference. Additionally, a deposit of 5D3 monoclonal antibody has been made at the American Type Culture Collection (ATCC), Rockville, Md, and is identified by ATCC Accession No. 40095.

As mentioned above, high-affinity monoclonal antibodies for the multi-determinant antigen being assayed are immobilized to a solid-phase immunoadsorbent in the simultaneous sandwich assay of this invention. There are many such solid-phase immunoadsorbents which have been employed. Well-known immunoadsorbents include beads formed from glass polystyrene, polypropylene, dextran, and other materials; tubes formed from or coated with such materials; etc. The antibody can be either covalently or physically bound to the solid-phase immunoadsorbent by techniques such as covalent bonding via an amide or ester linkage or adsorption. Those skilled in the art will know many other suitable solid-phase immunoadsorbents and methods for immobilized antibodies thereon, or will be able to ascertain such using no more than routine experimentation.

High-affinity monoclonal antibody is also used as the labeled antibody in the simultaneous sandwich assay described herein. Such antibodies can be labeled with a radioactive material, such as $^{125}I$; labeled with an optical label, such as a fluorescent material; labeled with an enzyme; or labeled by some other known technique.

The liquid sample, solid-phase immunoadsorbent with immobilized monoclonal antibody, and labeled soluble monoclonal antibody are incubated under conditions and for a period of time sufficient to allow antigen to bind to both the immobilized antibody and the labeled antibody. In general, it is usually desirable to provide incubation conditions sufficient to bind as much antigen as possible because this maximizes the binding of labeled antibody to the solid phase thereby increasing the signal. Typical conditions of time and temperature are two hours at 45° C. or twelve hours at 37° C.

Labeled antibody typically binds to antigen more rapidly than immobilized antibody since the former is in solution whereas the latter is bound to a solid-phase support. Because of this, labeled antibody should be employed in a lower concentration than immobilized antibody and it is also preferable to employ a high specific activity for labeled antibody. For example, labeled antibody might be employed at a concentration of about 1–50 ng/assay whereas immobilized antibody might have a concentration of 100–500 ng/assay. The labeled antibody might have a specific activity with, for instance, one iodine per IgM or as high as two labeled iodines per molecule of IgM angibody.

Of course, the specific concentrations of labeled and immobilized antibody, the temperature and time of incubation as well as other such assay conditions will depend upon many factors, including the specific antigen being assayed, the concentration of the antigen, and the monoclonal antibody or antibodies employed. Those skilled in the art will be able to determine operative and optimal assay conditions for each determination desired by employing routine experimentation.

After the single incubation period, the solidphase immunoadsorbent is removed from the incubation mixture. This can be accomplished by any of the known separation techniques, such as sedimentation or centrifugation. A washing step is not required prior to detection of bound labeled antibody. Detection can be performed by a scintillation counter, for example, if the label is a radioactive gamma emitter, or by a fluorometer, for example, if the label is a fluorescent material. In the case of an enzyme label, the detection can be done by colorimetric methods employing a competing substrate for the enzyme.

As noted above, results which have been achieved employing a simultaneous sandwich assay as described herein have demonstrated that such an assay can be more sensitive than forward and reverse sandwich assays wherein the total incubation time for each assay is the same. This is surprising, and the reason for such sensitivity is not well understood. While not wishing to be bound by this theory, one possible explanation is that the monoclonal IgM antibodies employed tend to form a crosslinked structure in the incubation mixture. Because of this, greater amounts of antigen and labeled antibody can be bound to the solid-phase immunoadsorbent. Data indicate, indirectly, for example, that more antigen molecules can bind to the solid phase than would be expected from the number of antibody molecules thus supporting the concept of crosslinking or layering.

Although data presented in the examples involves IgM antibodies, it is also believed that this simultaneous sandwich assay can employ IgG antibodies as either the immobilized or labeled antibody, or both. IgG molecules have two binding sites and are capable of crosslinking antigens.

The simultaneous sandwich assay of this invention will now be more specifically illustrated by way of the following examples.

EXAMPLE 1

Immunoradiometric Assay for HBsAg

Forward, reverse and simultaneous sandwich assays were compared for detection of HBsAg.

The monoclonal antibody employed in each was a monoclonal IgM antibody having high affinity for HBsAg and produced by the hybridoma cell line 5D3. The 5D3 hybridoma cell line comprises a cloned line developed by fusing the myeloma cell line P3-NS1/1-Ag4-1 derived from a BALB/c mouse MOPC 21 myeloma with mouse spleen cells immunized by a specific immunization procedure with HBsAg. The specific procedure employed is detailed in U.S. Pat. No. 4,271,145, the teachings of which are hereby incorporated by reference.

The solid-phase immunoadsorbent was provided by ¼ inch polystyrene beads obtained from Precision Plastic Ball Company, Chicago, Ill. The beads were coated with the monoclonal IgM antibody as follows. Ascites fluid derived from an immunized BALB/c mouse was diluted 1:500 to 1:5,000 in phosphate buffered saline (PBS). The beads were incubated for 16 hours at room temperature and washed three times with distilled water.

Monoclonal IgM antibody was labeled using the Bolten Hunter method. Specific activity ranged from about 2 to about 20 $\mu Ci/\mu$.

The forward sandwich assay protocol involved incubation of the beads having immobilized monoclonal IgM antibody thereon with 100 82 1 1% bovine albumin in PBS and 100 $\mu$l of an HBsAg-containing patient serum for one hour at 45° C. followed by washing three times with distilled water and subsequent addition of 200 μl of labeled antibody which was incubated for one hour at 45° C.

In the reverse sandwich assay protocol, 100 μl of labeled antibody were incubated with 100 μl of HBsAg-containing patient serum in a soluble phase for 1 hour at 45° C. Subsequently, monoclonal antibody coated onto the solid beads was added for an additional 1 hour at 45° C. The beads were subsequently washed three times with distilled water and placed in a scintillation counter.

The simultaneous sandwich assay protocol involved simultaneously incubating coated beads and 100 μl of labeled antibody and 100 μl of patient sample for two hours at 45° C. The beads were subsequently washed three times with distilled water and placed in a scintillation counter.

Additionally, patient samples were diluted a number of times by a factor of 10 and reassayed by each protocol to determine the limit of sensitivity for each assay protocol. A negative control consisting of human serum was employed.

The results are presented in Table 1. As can be seen from the data in Table 1, the simultaneous sandwich assay was more sensitive than either the forward or reverse assays where each assay employed the same monoclonal IgM antibody against HBsAg and wherein incubation conditions for each assay were the same.

TABLE I
COMPARISON OF REVERSE FORWARD AND SIMULTANEOUS SANDWICH ASSAYS USING A RADIOIMMUNO ASSAY

|  | FORWARD | | REVERSE | | SIMUL-TANEOUS | |
| --- | --- | --- | --- | --- | --- | --- |
|  | CPM | S/N | CPM | S/N | CPM | S/N |
| Negative Control | 407.2 | — | 149.6 | — | 63.5 | — |
| Patient Sample | 28,951 | 71.1 | 2,059 | 13.8 | 1,760 | 27.7 |
| 1:10 | 38,474 | 94.5 | 8,017 | 54.4 | 9,246 | 145.1 |
| 1:100 | 38,100 | 93.6 | 12,673 | 84.5 | 16,650 | 262.2 |
| 1:1000 | 11,892 | 29.2 | 8,091 | 53.9 | 8,725 | 137.4 |
| 1:10,000 | 2,921 | 7.2 | 1,840 | 12.3 | 2,311 | 36.4 |
| 1:100,000 | 799 | 1.9 | 361 | 2.4 | 1,024 | 16.1 |
| 1:1,000,000 | 546 | 1.3 | 99 | 0.66 | 582 | 9.2 |

NOTES
1. Data is expressed in Counts Per Minute (cpm's).
2. In all assays, identical number of total counts were added and identical reagents were used.
3. S/N in ratio of cpm in sample divided by cpm is negative control. A S/N of greater than 2.0 represents a positive.

EXAMPLE 2
Clinical Patient Study

A comparative clinical patient study was made employing 290 patient samples collected at Massachusetts General Hospital from different sources. The simultaneous sandwich assay employed is the one described in Example 1. Commercial assays employed are noted. The results were:

TABLE II

| Patient Group | (1) No.Pos. SSA | (2) No.Pos. Comm. | (3) No.Pos. Anti-HBc | (4) No.Pos. Anti-HBs | Total No. Studied |
| --- | --- | --- | --- | --- | --- |
| Acute hepatitis B | 42 | 42 | 36 | — | 42 |
| Acute hepatitis | 12 | 0 | 6 | 6 | 22 |
| Post-Transfusion hepatitis | 9 | 0 | 6 | 3 | 25 |
| Blood donors | 5 | 1 | 3 | 0 | 92 |
| Alcoholic liver disease | 2 | 0 | 2 | 0 | 50 |
| Normal controls | 0 | 0 | 6 | 7 | 59 |
| | | | | Total | 290 |

1. Simultaneous sandwich assay
2. Abbott Ausria II assay
3. Abbott Corab assay
4. Abbott Ausab assay
5. Anti-HBc titer > 1:1024 on 2 positives in SSA It should be noted that the SSA detected postive samples in cases of acute hepatitis and post-transfusion hepatitis whereas the commercial assay produced negative results.

INDUSTRIAL APPLICABILITY

The invention described herein is useful in the detection of multi-determinant antigens, such as hepatitis B surface antigen (HBsAg). Thus, the assay can be employed by hospitals or clinical laboratories for the early detection of viral infection or the presence of non-viral antigens.

EQUIVALENTS

Those skilled in the art will recognize, or be able to ascertain, using no more than routine experimentation, many equivalents to the specific embodiments of the invention described herein. Such equivalents are intended to be encompassed by the following claims.

We claim:
1. In an immunoassay for detecting the presence of a multi-determinant antigen in a liquid sample wherein said sample is simultaneously incubated in the presence of an immunoadsorbent containing immobilized antibody for said antigen and labeled antibody for said antigen, and thereafter detecting the amount of labeled antibody bound to said immunoadsorbent as an indication of the amount of antigen present in said sample:
    the improvement wherein said immobilized antibody and said labeled antibody comprise high-affinity IgM monoclonal antibodies directed against a multiply-appearing determinant of said antigen.
2. The improvement of claim 1 wherein said labeled monoclonal antibody and said immobilized monoclonal antibody comprise the same monoclonal antibody.
3. The improvement of claims 1 or 2 wherein said antigen is a viral antigen comprising a virus or antigenically-active portion thereof.
4. The improvement of claim 3 wherein said viral antigen comprises an hepatitis viral antigen.
5. The improvement of claim 4 wherein said hepatitis viral antigen comprises HBsAg.
6. An immunoassay for detecting the presence of a multi-determinant antigen in a liquid sample comprising:
    a. forming an incubation mixture containing:
        i. liquid sample:
        ii. a solid-phase immunoadsorbent containing immobilized high-affinity IgM monoclonal antibody directed against a multiply-appearing determinant of said antigen; and,
        iii. labeled, soluble, high-affinity, IgM monoclonal antibody directed against a multiply-appearing determinant of said antigen;

b. incubating said incubation mixture under conditions and for a period of time sufficient for antigen in the liquid sample to bind to both immobilized monoclonal antibody and labeled, soluble, monoclonal antibody;

c. separating said solid-phase immunoadsorbent from the incubation mixture after said incubation; and, d. detecting for labeled monoclonal antibody bound to said solid-phase immunoadsorbent as an indication of the amount of said antigen in the liquid sample.

7. An immunoassay of claim 6 wherein said labeled, soluble monoclonal antibody and said immobilized monoclonal antibody comprise the same monoclonal antibody.

8. An immunoassay of claims 6 or 7 wherein said multi-determinant antigen is a viral antigen comprising a virus or antigenically-active portion thereof.

9. An immunoassay of claim 8 wherein said viral antigen comprises an hepatitis viral antigen.

10. An immunoassay of claim 9 wherein said hepatitis viral antigen comprises HBsAg.

11. An immunoassay of claim 10 wherein said labeled, soluble, monoclonal antibody contains a radioactive label.

12. An immunoassay of claim 11 wherein said radioactive label comprises $^{125}$I.

13. An immunoassay of claim 10 wherein said labeled, soluble, monoclonal antibody is labeled with an enzyme label.

14. An immunoassay of claim 10 wherein said labeled, soluble, monoclonal antibody is labeled with an optical label.

15. An immunoassay of claim 14 wherein said optical label comprises a fluorescent material.

* * * * *